United States Patent [19]

Culbert

[11] Plant 4,217

[45] Feb. 21, 1978

[54] CHRYSANTHEMUM PLANT

[75] Inventor: John Robert Culbert, Monticello, Ill.

[73] Assignee: University of Illinois Foundation, Urbana, Ill.

[21] Appl. No.: 773,978

[22] Filed: Mar. 3, 1977

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Merriam, Marshall & Bicknell

[57] ABSTRACT

A novel chrysanthemum characterized by long lasting blossoms having spooned, white ray florets enclosing a yellow anemone center.

2 Drawing Figures

1

The present invention relates to a new and distinct cultivar of chrysanthemum plant asexually reproduced by cuttings from a seedling selected from among the progeny of the cross of unpatented parent plants selected from among the stocks maintained by the Department of Horticulture, University of Illinois, Urbana, Ill., and identified for breeding purposes as Nos. 32-01-69 and 44-02-67.

Successive propagations of my new cultivar have retained the distinctive unique characteristics thereof, to wit:

1. Flowers of anemone form consisting of 1 to 2 rows of white spooned ray florets arranged loosely and encircling a cushion of yellow disc florets;

2. Flowers are 3½" to 4" in diameter when produced on a pinched plant and disbudded to 1 flower per stem; flowers are 2" to 3" in diameter when produced on a pinched plant and grown in a spray of several flowers per stem;

3. Flowering response of approximately 7½ to 9 weeks from start of initiation dependent upon whether grown disbudded or in a spray and upon season of year;

4. Ray florets open relatively quickly followed by the relatively slow opening of the disc florets which results in a long "shelf life" or keeping quality since the ray florets maintain their form as the disc florets continue their development to maturity;

5. Strong plants that produce 3 to 5 breaks per pinched plant.

My new cultivar, when grown in the vicinity of Urbana, Ill., has a flowering response period of approximately 7½ to 9 weeks from the start of initiation, and the following detailed description is based on observations made of the new cultivar in the Ornamental Horticulture greenhouses in Urbana, Ill. The flowering response time of disbudded flowers may be from 3 to 7 days earlier than that of flowers grown as a spray. The response time, blooming period, color, relative number of ray and disc florets, flower size, and total vigor may vary significantly with varying environmental conditions such as temperature, day length, light intensity and amount of carbon dioxide in the greenhouse atmosphere.

The flowering chart outlines the variation of flowering response pattern for flowers produced on pinched plants grown in spray form experienced for the various seasons in Urbana, Ill.

2

| Months | Flowering response pattern for pinched plants grown in spray form at Urbana, Il. |
|---|---|
| April, May, June | 8 weeks |
| July through mid-September | late 9 weeks |
| Mid-September through November | 8 weeks |
| December through March | early 9 weeks |

Suggested period for fowering in the north central United States is year round. Some delay in flowering may be experienced in the above area from July through mid-September during extremely high temperatures.

The accompanying drawing shows the unique characteristics of my new cultivar, the color being as nearly true as possible with color illustrations of this type.

FIG. 1 photographically illustrates blooms of my cultivar grown as a spray of several flowers per stem.

FIG. 2 photographically illustrates blooms of my cultivar grown on a plant which was disbudded to one flower per stem. Color references are made to the Nickerson Color Fan published by Munsell Color Co., 1957.

Botanical classification: *Chrysanthemum morifolium* Ramat.

Bloom:

*Size.*—(When disbudded and fully expanded): 3½" to 4"; (when grown as a spray and fully expanded): 2" to 3".

*Depth.*—(When disbudded and fully expanded): ½" to ¾"; (when grown as a spray and fully expanded): ⅜" to ½".

*Form.*—Anemone type; the 20 to 45 ray florets are arranged in 1 to 2 rows about the cushion which forms the center of the composite flower head and which consists of 175 to 225 disc florets set closely together; both ray and disc florets are attached to a common receptacle; the ray florets elongate first and assume a position at approximately right angles to the pedicel as they develop; the outer disc florets elongate next, followed successively by the inner florets; when fully expanded the flower head appears as a rounded mound or cushion of the disc florets surrounded by the 1 or 2 rows of ray florets.

*Borne.*—Clusters on pedicels which are ½" to 2" long.

*Stems.*—Strong.

*Permanence.*—14 to 21 days.

Petals (ray florets):

*Color.*—White.

*Form.*—Tubular; flaring and opening to spoon form at tip tapering to a blunt point.

*Size.*—(When disbudded and fully expanded): length of tube: 1" to 1¼"; length of spoon: ⅛" to ¾"; diameter of tube: ⅛"; diameter of spoon: ¼" to 7/16". (When grown as a spray and fully expanded): length of tube: ¾" to 1"; length of spoon: ⅛" to ½"; diameter of tube: ⅛"; diameter of spoon: 3/16" to 5/16".

*Number.*—Average number 30 (range 20 to 45).

*Arrangement.*—In 1 to 2 rows along outer edge of receptacle.

*Texture.*—Smooth.

*Persistence.*—Resists shattering.

Disc florets:

*Color.*—Unopened: vivid greenish yellow, 7.5 Y 8/12. Immediately on opening: brilliant yellow, 5 Y 9/9. Partially mature: ivory, 10 YG 9/2. Fully mature: white.

*Form.*—Tubular; opening at end to form a 5-pointed star.

*Size.*—(When disbudded and fully expended): Individual florets: length: ½" to ⅞" diameter of tube: 1/16" diameter of open end: ⅛". Cushion made up of all the disc florets: diameter: 1½" to 1¾". (when grown as a spray and fully expanded): Individual florets: length: ⅜" to ⅝"; diameter of tube: 1/16"; diameter of open end: ⅛". Cushion made up of all the disc florets: diameter: 1" to 1¼".

*Number.*—175 to 225.

*Fragrance.*—Sweetish, somewhat resembling that of honey; not strong.

*Persistence.*—Strongly resists shattering.

Reproductive organs:

*Stamens, anthers.*—Epipetalous and syngenesious in disc florets. Number: 875 to 1125. Pollen: plentiful; Color: vivid yellow, 2.5 Y 8/12.

*Pistil.*—Style: number — 1 per each ray or disc floret; length — short. Stigma: number — 2 per each style. Ovary: position — at base of ray or disc floret attached to receptacle.

Plant:

*Form.*—Herbaceous perennial.

*Growth.*—Somewhat spreading.

*Height.*—Average height 11" (range 8" to 14") when pinched and given 9 week medium treatment during the various seasons of the year.

*Spread.*—Average spread 8" (range 6" to 10") per plant when pinched and given 9 week medium treatment during the various seasons of the year.

*Foliage.*—Color: top side — moderate olive green, 7.5 GY 4/4; bottom side — moderate yellow green, 7.5 GY 5/7; Size: average length 3"; average width 2"; range: length 1" to 4"; width ⅝" to 2½". Quantity: 12 to 14 leaves per 6" stem when pinched and given 9 week medium treatment during the various seasons of the year. Shape: simple, obovate. Margin: moderately lobed, crenate. Base: hastate. Apex: obtuse. Venation: pinnate, moderately prominent. Texture: coarse. Stipules: rudimentary.

What is claimed is:

1. A new and distinct cultivar of chrysanthemum plant substantially as herein shown and described, characterized particularly as to novelty by anemone type flowers consisting of white spooned ray florets loosely arranged in 1 to 2 concentric rows about the yellow cushion of disc florets which results in the dainty, airy, bicolor appearance of the flowers, by the slow development of the flowers which remain attractive from their youngest open stage past full maturity resulting in long "shelf life", by the versatile nature of the flowers in that they may be grown either disbudded for increased size or in sprays for increased production of smaller flowers, by flower buds which develop normally in from 7½ to 9 weeks from start of initiation throughout the year, and by strong, leafy plants which average 3 to 5 breaks per pinched plant making a showy display of 3½" to 4" disbudded flowers or of 2" to 3" flowers borne in sprays.

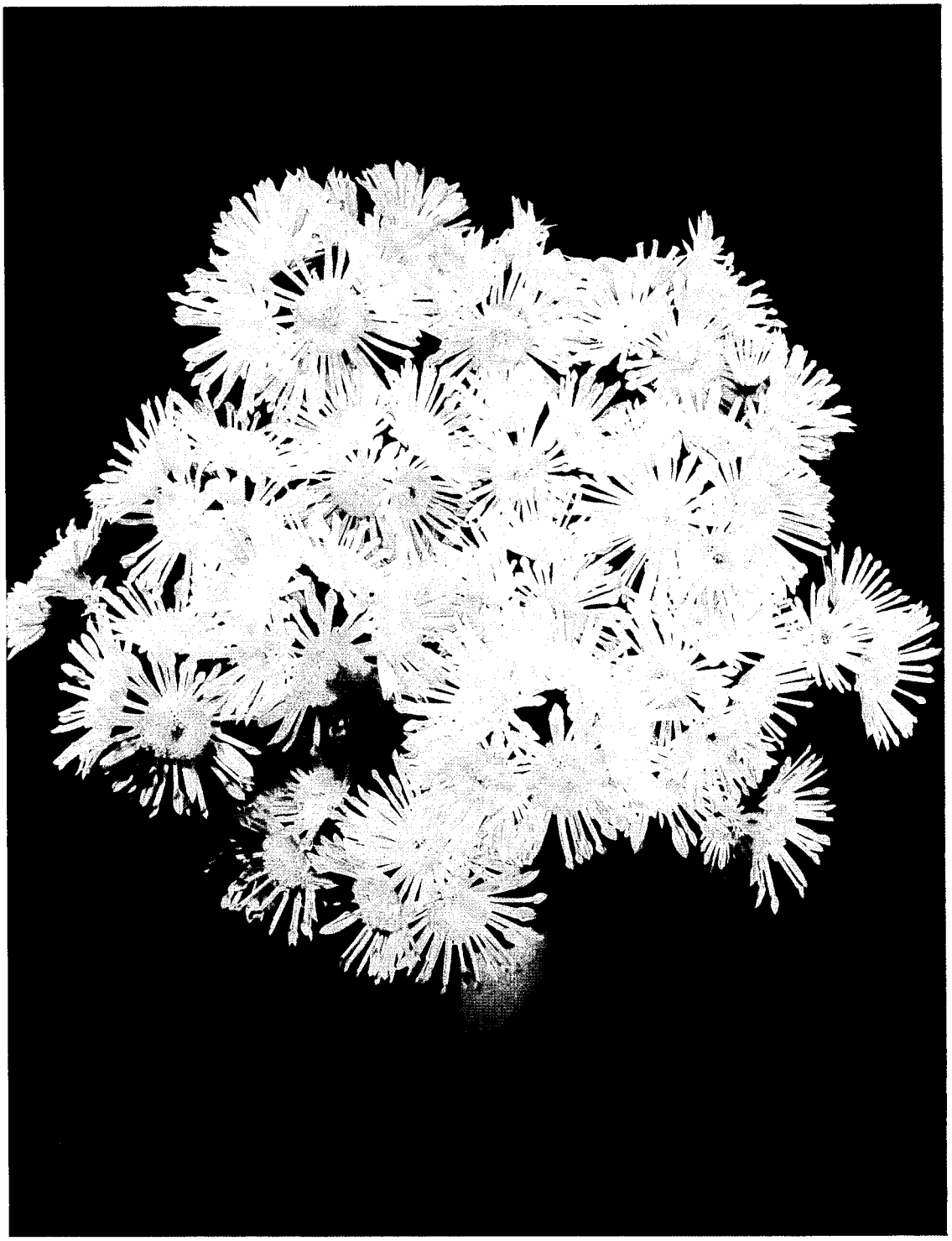

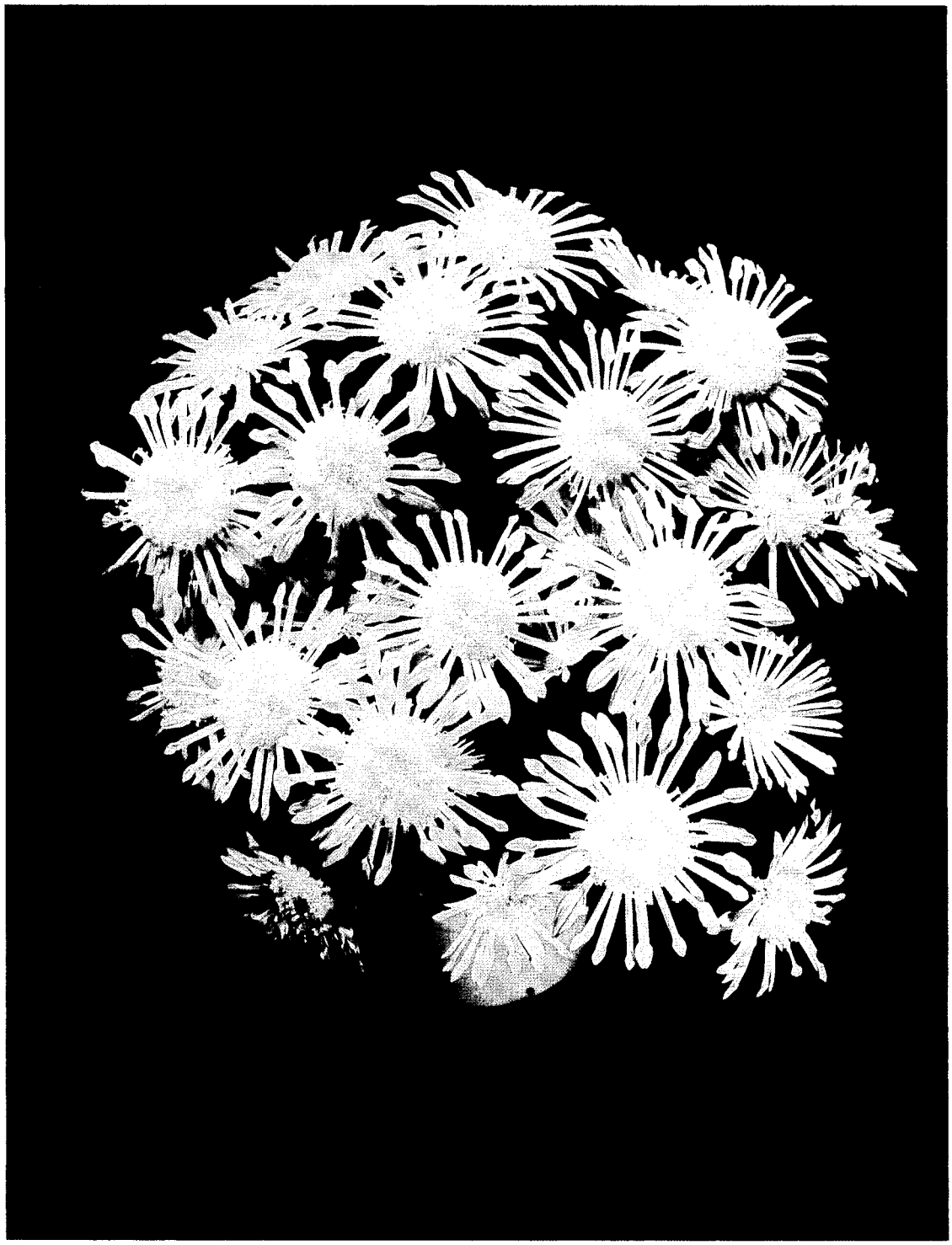

* * * * *